United States Patent [19]

Momose et al.

[11] Patent Number: 5,133,750
[45] Date of Patent: Jul. 28, 1992

[54] SYNTHETIC SAPPHIRE INTRAOCULAR LENS

[76] Inventors: Akira Momose, 1-100 Umeda, Kiryu, Japan, 376-06; Adam A. Taff, 15 Jacobs Rd., Thiells, N.Y. 10984

[21] Appl. No.: 652,981

[22] Filed: Feb. 11, 1991

Related U.S. Application Data

[63] Continuation-in-part of Ser. No. 522,139, May 11, 1990, abandoned.

[51] Int. Cl.$^5$ .............................................. A61F 2/16
[52] U.S. Cl. ...................................... 623/6; 623/901; 65/33; 501/86
[58] Field of Search ................... 623/6, 901; 63/32; 65/33; 501/86

[56] References Cited

U.S. PATENT DOCUMENTS

| | | | |
|---|---|---|---|
| 2,634,554 | 4/1953 | Barnes | 65/33 X |
| 3,996,627 | 12/1976 | Deeq et al. | 632/6 |
| 4,079,470 | 3/1978 | Deeq et al. | 623/6 |
| 4,249,271 | 2/1981 | Poler | 623/6 |
| 4,480,340 | 11/1984 | Shepard | 623/6 |
| 4,880,427 | 11/1989 | Ais | 623/6 |

Primary Examiner—Ronald Frinks
Attorney, Agent, or Firm—Singer & Singer

[57] ABSTRACT

There is disclosed a new and improved intraocular lens (IOL) for use by surgeons as a replacement for a person's cataractous lens. The disclosed lens is a synthetic sapphire lens having either a silicone or polyimide haptic thereby making the lens autoclavable. The lens is resistant to damage caused by YAG laser and eliminates the need for ridges of any kind on the surface of the lens which has previously been used to keep the lens off the posterior capsule of the crystalline lens. Eliminating the need for a ridge now allows the lens to be made much thinner and also eliminates the tiddlywink effect. The new IOL is approximately ⅓ to 1/5 the thickness of standard PMMA IOLs and is totally non-degradable.

6 Claims, 1 Drawing Sheet

SYNTHETIC SAPPHIRE INTRAOCULAR LENS

This is a continuation in part of Patent Application Ser. No. 07/522,139, Filed May 11, 1990 and now abandoned.

This invention relates to an improved intraocular lens called an IOL and more particularly to a synthetic sapphire ($AL_2O_3$) optic in combination with a haptic that now allows the IOL to be autoclavable. Also disclosed is a method for implanting the IOL.

In the art as practiced today, the IOL has found great popularity among ophthalmologists and patients alike for the treatment of cataracts which have the effect of inhibiting the patient from normal sight due to clouding over the human crystalline lens.

In the normal eye, the crystalline lens is encased within a capsule and held by a plurality of strands called zonules that are in turn attached to ciliary muscles in the ciliary body on the inner wall of the eyeball. The zonules in effect comprise a plurality of strands that radiate from the periphery of the capsule and tend to hold the capsule in the center, thereby helping to center the capsule within the eye and at the same time allow the capsule and the lens to move and focus in response to objects at various distances.

A cataract condition is defined as a general loss of transparency or cloudiness of the crystalline lens which is located within the capsule thereby preventing light from passing through to the retina. The capsule is divided into two portions, i.e. the anterior capsule which covers the front of the nucleus of the crystalline lens and the posterior capsule which covers behind the nucleus.

The present day treatment for cataract involves the cutting of the anterior capsule coupled with the removal of the clouded nucleus and the cortex of the lens located within the capsule. The surgeon leaves the posterior portion of the capsule in place and insures that all portions of the cortex and the nucleus of the opaque crystalline lens have been removed.

Present day implantation technique favors the use of posterior placement which means that the IOL is implanted behind the iris and in close proximity to the posterior capsule. However, in some instances, the IOL has to be implanted in front of the iris, i.e. anterior placement.

After cataract removal and IOL implantation, a certain enzyme called T-nonpearls tend to migrate between the posterior surface of the IOL and the posterior capsule. The T-nonpearls deleteriously effect the posterior capsule by making it opaque and they also interfere with the light transmission into the patient's eye. This condition is called after cataract. The common treatment for removing after cataract is to use a laser known as YAG laser.

The YAG laser is an extremely powerful laser that is focused on the posterior capsule and is designed to break the capsule where it has gone opaque, thereby allowing light to again pass through to the retina. Unfortunately, the effect of the YAG laser also destroyes the IOL itself.

IOLs have many variations in design and as a result different surgical techniques of lens placement have evolved. Presently, the industry is using polymethylmethacrylate (PMMA), silicone and HEMA for optics, nylon or polypropylene for haptics.

Unfortunately, the use of lasers in after cataract surgery has resulted in damage to the sensitive plastic materials of the IOL, leaving large pits and stress cracks. Obviously, these cracks and pits impair the vision of the patient which resulted in the work done by Drs. Hoffer and Fritch in attempting to raise the IOL from contacting the posterior capsule.

The next important development in the art resulted from the efforts of Dr. Kenneth Hoffer of Santa Monica who designed an IOL lens implant with a ring in the form of a shoulder or ridge completely around the posterior surface edge of the IOL. The shoulder was originally designed to prevent the migration of the T-nonpearls. The effectiveness of the shoulder to stop migration of the T-nonpearls is not generally accepted by the authorities in the field, however, the ridge designed by Dr. Hoffer did have the effect of maintaining a distance between the posterior surface of the IOL and the capsule. The space between the IOL and the posterior capsule allows the ophthalmologists to use the YAG laser to break the opaque posterior capsule, i.e. after cataract caused by T-nonpearls without destroying or damaging the IOL.

Unfortunately, the shoulder or ridge located on the posterior surface of the IOL created additional problems for the surgeon when inserting the IOL. Specifically, the incision must be made larger to allow the ridge to pass through and thereby possibly causing additional trauma to the eye and when grasping the IOL with his forceps, it is almost impossible for the surgeon to properly grasp the IOL during surgery, because of the ridge.

During the operation of inserting the IOL, the ridge causes the lens to move or tiddle. This phenomena has been called tiddlywink by those skilled in the art and refers to any uncontrolled movement of the lens while being held in position by the surgeon during insertion of the implant in the eye. Obviously the tiddlywink effect is very dangerous for the eye.

Lastly, insertion of the IOL with the shoulder into the posterior chamber of the eye which is behind the iris means that the ridge of the IOL on one side must pass over the iris once and then the other side of the ridge must pass over the iris again when finally being inserted in place. As a result, the iris is teased twice in the process.

Considering that the iris is a very sensitive tissue, it can be appreciated that the ridge on the IOL has the effect of traumatizing the iris as the ridge passes over the iris when located in place by the surgeon because the iris is easy to bleed or even to rip during the operation. In many cases, this traumatizing of the iris has caused the pupil to contract during the operation even though the pupil has been previously dilated with a suitable mydriatics such as tropicamide or cyclopentolate, thereby making it difficult for the surgeon to continue the operation.

The next important contribution to the design of IOL is the work of Dr. Charles D. Fritch who disclosed an improved IOL in his U.S. Pat. No. 4,685,920 issued Aug. 11, 1987. The Fritch invention represents an improvement over the work done by Dr. Hoffer in that the shoulder or ridge is now constructed in two half arcs tapering from a minimum to a maximum and back to a minimum, thereby allowing the surgeon to grasp the IOL between the two arcs. This eliminates the tiddlywink effect and the cam surface of the ridge allows the IOL to slide over the iris smoothly during insertion thereby minimizing any damage and trauma to the eye.

The Fritch improvement has been widely accepted and is in use today and represents a distinct contribution over the work of Dr. Hoffer, however even the Fritch device still has ridges that must slide over the iris and the danger of damage and traumatization to the iris is still present even though the effect has been minimized.

Approximately ten years ago, a company called Lynell Medical Technology Corporation introduced and produced a glass IOL. A polyimide haptic was attached to the glass optic, The original glass lens was intended to be implanted in the posterior chamber. Unfortunately, their IOL was susceptible to damage by pitting and cracking when subjected to the large intensity of energy of a YAG laser. The use of glass was then discontinued in favor of the then new plastic IOL having a ridge or shoulder.

All these prior art techniques met with some success; however, the problem still remains and will not be eliminated until all IOLs are made in accordance with the present invention from synthetic sapphire material with haptics that are either polyimide or silicone.

A patent issued to Deeg et al on Mar. 21, 1978 and entitled Artificial Intraocular Lens discloses the advantages of using an inert material for an IOL such as sapphire. While the benefits of using a sapphire inert material as an IOL are described, there is no indication of how to grow the sapphire so that it can be cut, polished and assembled as an IOL The processing of the sapphire is critical for the sapphire to be laser proof. A reference to the Barnes U.S. Pat. No. 2,634,554 will show that the sapphire crystal may be cut from any angle from 0 to 90 degrees.

What the Barnes patent and the Deeg patent do not teach is the fact that if the sapphire is sliced at 90 degrees relative to the angle of growth of the sapphire, it is very easy to polish but is very weak and fragile. On the other hand if the sapphire is sliced at 0 degrees relative to the angle of growth, the sapphire is very strong but impossible to polish.

The present invention is concerned primarily with an IOL that eliminates the need of ridges taught by Hoffer or the bifurcated ridges as taught by Fritch, and because of the nature of the material used, the IOL can now be made one third to one fifth (the central thickness of 7.0 mm PMMA lens is 1.5 mm) the thickness of previously made and hence, requires a smaller incision.

Also an immediate unobvious advantage is that it is now possible to make a lens having a convex surface on both sides rather then one limited to one having a plano surface on one side and a convex surface on the other, thereby allowing the new thin lens to make a smooth insertion into the posterior chamber without damaging the iris.

The benefits claimed by this invention are obtained by constructing the intraocular lens of a synthetic sapphire material known generally as $Al_2O_3$ together with a haptic made either of polyimide or silicone. The need for a ridge or shoulder is eliminated since the synthetic sapphire is not damaged by the use of the YAG laser.

In the preferred embodiment the sapphire is sliced at an angle between 10 degrees and 45 degrees to produce an eliptical blank that is then centerless ground to make a specific diameter blank of approximately 5 mm. or any other desired size. The blank is then ground and polished to obtain a highly polished surface. It is then cleaned and checked for correct power and tested for laser stability after which it is assembled, formed and cleaned again before being packaged.

The method of inserting the lens is now improved since the thickness of the lens is reduced allowing the surgeon to implant the IOL through a smaller incision and in direct contact with the capsule.

Further objects and advantages of the present invention will be made more apparent by referring now to the accompanying drawing wherein.

Intraocluar lens have many variations in design and as a result different surgical techniques and lens placement techniques have evolved. Presently the industry is now using polymethylmethacrylate (PMMA) silicone and HEMA for optics and PMMA, nylon or polypropylene for haptics.

Unfortunately, the use of lasers in after cataract surgery has resulted in damage to the sensitive plastic materials of the IOL leaving large pits and stress cracks. Obviously these cracks and pits impair the vision of a patient which resulted in the work done by Drs. Hoffer and Fritch in attempting to raise the IOL from contacting the posterior portion of the capsule.

Unfortunately, these ridges used on the IOL required a great skill in the hands of the surgeon since focusing of the YAG laser is extremely critical which sometimes resulted in damage to both the capsule and plano surface of the IOL. The use of a spider haptic was designed specifically to improve the holding of the IOL and thereby minimize the criticalness in the focusing of the YAG laser during after cataract operations.

The synthetic sapphire, also known as $AL_2O_3$ Corundum, when processed for crystal growing would yield a laser resistant material highly suitable for IOLs. It has been determined that the axis in which the axis is grown, cut and processed into an optic is highly critical in obtaining the laser resistant characteristics. For example, reference is made to U.S. Pat. Nos. 1,004,505 by Verneuil and 2,634,554 by M. B. Barnes. Experimentation has shown that processing the material at angles ranging from 10 degrees to 45 degrees is critical to produce an optic highly resistant to laser bombardment.

The sapphire material has unsurpassed optical qualities and strength, and is biologically stable and inert and has the ability to be sterilized by autoclaving. The sapphire optic and polyimide optic can be formed into a vast variety of IOL styles limited only by the imagination of the surgeon and the manufacturer.

The sapphire optic has a higher refractive index (1.78) than PMMA (1.49) and has a superior resolving power than present day plastic lenses and is less than 0.3 mm thick as compared to a PMMA lens thickness of 0.7 to 1.5 mm. This aspect alone provides for ease of implantation, stability and avoidance of injury to sensitive tissues in the eye. The polyimide haptic is very thin (0.076 mm) as compared to PMMA or PROLENE (polypropylene) that is 0.150 mm thick or more. It is also flexible enough to prevent trauma to intraocular tissue at the time of insertion.

Both the sapphire and the polyimide have undergone the FDA recommended toxicity, and biocompatible studies which show them to be nontoxic and biocompatible.

Figure 1:
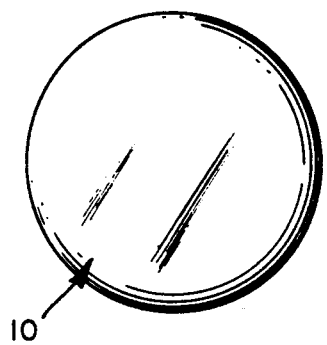
FIG. 1 is a plan view of an optic constructed of synthetic sapphire material.
Figure 2:
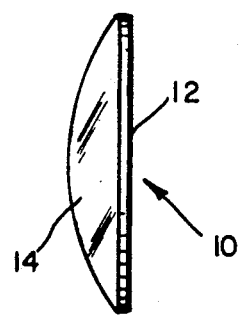
FIG. 2 is a side view of the lens illustrated in FIG. 1 illustrating the convex and the plano surface.
Figure 3:
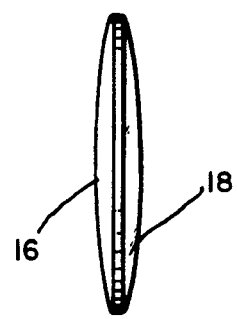
FIG. 3 is a side view of a synthetic sapphire optic having a convex surface on both sides.

Referring now to FIGS. 1 and 2, there is shown a sapphire optic 10 that is substantially circular in cross section and which has a plano surface 12 on one side and a convex surface 14 on the other side. It will be understood that the optic can be of any shape, that is, bi-convex as required by the surgeon. FIG. 3 illustrates a lens constructed according to the present invention in which both sides have convex sides 16 and 18.

Figure 4:
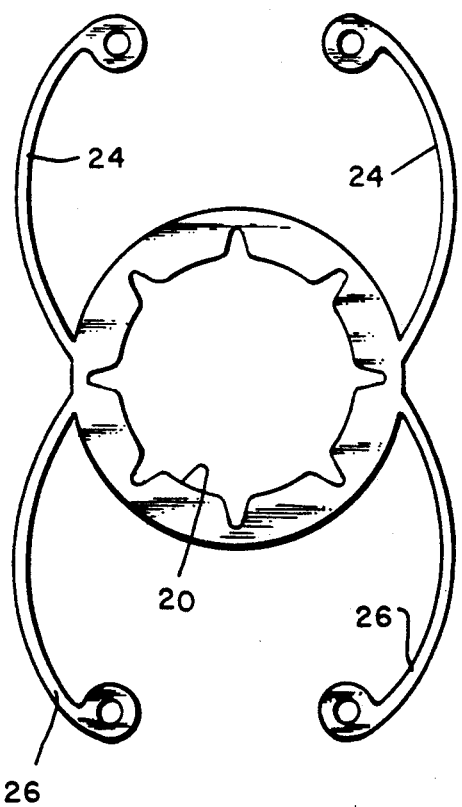
FIG. 4 is a plan view of a synthetic sapphire IOL lens in combination with a polyimide haptic constructed according to the teaching of the present invention.

Referring now to FIG. 4 there is shown a synthetic sapphire 20 in combination with haptic pairs of arcuate arms 24 and 26. This design of the IOL can be implanted very smoothly into the posterior chamber as well as into the anterior chamber. The defined structure of spider design provides a special benefit of easy insertion either before the iris (Anterior Chamber) or after the iris (Posterior Chamber).

Figure 5:
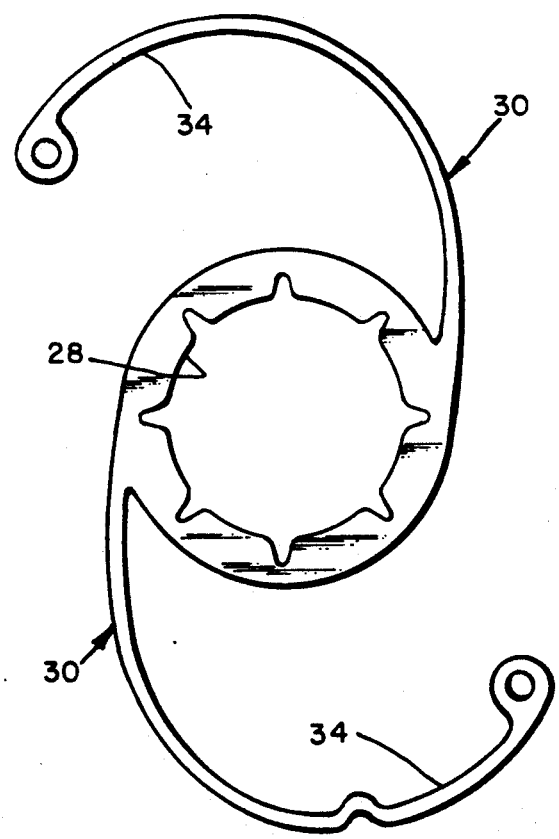
FIG. 5 is a plan view of a second embodiment of a synthetic sapphire IOL in combination with a polyimide haptic.

Referring now to FIG. 5, there is shown a synthetic sapphire IOL in combination with C-loop haptic, with arcuate arms 30 and 34. This design of the IOL can be implanted into the posterior chamber very smoothly.

The defined structure of the C-loop haptic provides neat and smooth insertion into the posterior chamber.

In addition, the IOL and haptic eliminates the incidence of after cataract formation, because the materials are inert and cover the posterior capsule tightly, not allowing the T-nonpearls to migrate. As mentioned previously, the IOL materials are autoclavable which means they can be steam sterilized which is the most effective method of sterilization.

We claim:

1. An improved lens implant comprising:
    an optic constructed of synthetic sapphire material cut at an angle of between 10 degrees to 29 degrees to the angle of growth in combination with a haptic whereby said material makes said lens impervious to damage by YAG laser activity;
    said angle of growth being positioned that the crystallographic orientation with respect to the growth axis of the growing body is the same as the crystallographic orientation initially desired;
    said optic having a pair of opposing surfaces forming a lens.

2. An improved lens implant according to claim 1 in which one of said surfaces is plano and the other surface is convex.

3. An improved lens implant according to claim 1 in which both of said surfaces are convex.

4. An improved lens implant according to claim 1 in which said haptic is constructed of polyimide thereby making the complete implant autoclavable.

5. An improved lens implant according to claim 1 in which both sides of said optic are smooth without the need of rings of any kind thereby providing a smooth surface for holding the lens without the tiddlywink effect.

6. A method of constructing an inert sapphire optic that comprises the steps of;
    cutting a sapphire crystal at an angle of between 10 degrees and 29 degrees to the angle of growth to produce an eliptical blank, and
    said angle of growth being positioned that the crystallographic orientation with respect to the growth axis of the growing body is the same as the crystallographic orientation initially desired; and
    then grinding and polishing the blank to a desired diameter.

* * * * *

UNITED STATES PATENT AND TRADEMARK OFFICE
CERTIFICATE OF CORRECTION

PATENT NO.  : 5,133,750
DATED       : Jul. 28,1992
INVENTOR(S) : Akira Momose & Adam A. Taff It is certified that error appears in the above-identified patent and that said Letters Patent is hereby corrected as shown below:

On the title page, Item [56]:

Cited Patent 4,880,427 : Inventors name should be -Anis-

Column #4 Line 57: the word "optic" should be -haptic-

Signed and Sealed this

Twenty-first Day of September, 1993

*Attest:*

BRUCE LEHMAN

*Attesting Officer*   *Commissioner of Patents and Trademarks*